United States Patent [19]

Fein et al.

[11] Patent Number: 5,779,630
[45] Date of Patent: Jul. 14, 1998

[54] MEDICAL SENSOR WITH MODULATED ENCODING SCHEME

[75] Inventors: Michael E. Fein, Mountain View; David C. Jenkins, Loomis; Michael J. Bernstein, San Ramon; K. L. Venkatachalam, Palo Alto; Adnan I. Merchant, Fremont; Charles H. Bowden, San Ramon, all of Calif.

[73] Assignee: Nellcor Puritan Bennett Incorporated, Pleasanton, Calif.

[21] Appl. No.: 451,630

[22] Filed: May 26, 1995

Related U.S. Application Data

[62] Division of Ser. No. 168,449, Dec. 17, 1993, Pat. No. 5,695,059.

[51] Int. Cl.$^6$ ............................................... A61B 5/00
[52] U.S. Cl. ................................ 600/323; 600/331
[58] Field of Search .......................... 128/633, 664–665; 340/870.15; 375/236; 370/870.15; 600/310, 323–332

[56] References Cited

U.S. PATENT DOCUMENTS

| | | |
|---|---|---|
| 3,790,910 | 2/1974 | McCormack. |
| 3,910,701 | 10/1975 | Henderson et al. |
| 4,178,549 | 12/1979 | Ledenbach et al. ............ 375/238 |
| 4,253,071 | 2/1981 | Underhill et al. |
| 4,303,984 | 12/1981 | Houvig. |
| 4,362,935 | 12/1982 | Clark, III. |
| 4,384,773 | 5/1983 | Hambly. |
| 4,418,392 | 11/1983 | Hata. |
| 4,446,715 | 5/1984 | Bailey. |
| 4,468,562 | 8/1984 | Wicnienski et al. |
| 4,621,643 | 11/1986 | New Jr. et al. ............ 128/633 |
| 4,636,934 | 1/1987 | Schwendemann et al. |
| 4,684,245 | 8/1987 | Goldring. |
| 4,700,708 | 10/1987 | New, Jr. et al. |
| 4,759,369 | 7/1988 | Taylor. |
| 4,770,179 | 9/1988 | New, Jr. et al. |
| 4,840,066 | 6/1989 | Bostco et al. |
| 4,846,183 | 7/1989 | Martin. |
| 4,858,615 | 8/1989 | Meinema. |
| 4,897,854 | 1/1990 | Harris et al. |
| 4,911,167 | 3/1990 | Corenman et al. |
| 4,915,639 | 4/1990 | Cohn et al. |
| 4,918,296 | 4/1990 | Fujisaka et al. |
| 4,930,506 | 6/1990 | Ullrich. |
| 4,942,877 | 7/1990 | Sakai et al. |
| 4,947,033 | 8/1990 | Kordts et al. |
| 4,972,470 | 11/1990 | Farago. |
| 5,058,588 | 10/1991 | Kaestle. |
| 5,078,136 | 1/1992 | Stone et al. |
| 5,181,858 | 1/1993 | Matz et al. |
| 5,193,543 | 3/1993 | Yeldermen ............ 128/693 |
| 5,202,682 | 4/1993 | Finger ............ 340/870.19 |
| 5,209,235 | 5/1993 | Brisken et al. |
| 5,222,164 | 6/1993 | Bass, Sr. et al. |
| 5,351,685 | 10/1994 | Potratz. |
| 5,560,355 | 10/1996 | Merchant et al. |
| 5,575,285 | 11/1996 | Takanashi et al. |
| 5,645,059 | 7/1997 | Fein et al. |

FOREIGN PATENT DOCUMENTS

| | | |
|---|---|---|
| 2595561 | 9/1987 | France. |
| WO 92/21281 | 12/1992 | WIPO. |
| WO 93/06776 | 4/1993 | WIPO. |

*Primary Examiner*—Robert L. Nasser
*Attorney, Agent, or Firm*—Townsend and Townsend and Crew LLP

[57] ABSTRACT

The present invention provides an encoding mechanism for a medical sensor which uses a modulated signal to provide the coded data to a remote analyzer. The modulated signal could be, for instance, a pulse width modulated signal or a frequency modulated signal. This signal is amplitude independent and thus provides a significant amount of noise immunity.

15 Claims, 5 Drawing Sheets

MEDICAL SENSOR WITH MODULATED ENCODING SCHEME

This is a division of application Ser. No. 08/168,449 filed Dec. 17, 1993, now U.S. Pat. No. 5,695,059.

BACKGROUND OF THE INVENTION

The present invention relates to medical sensors which include coded calibration information relating to characteristics of the sensor.

An example of such an encoding mechanism is shown in U.S. Pat. No. 4,700,708. This relates to an optical oximeter probe which uses a pair of light emitting diodes (LEDs) to shine light through a finger, with a detector picking up light which has not been absorbed by oxygen in the blood. The operation depends upon knowing the wavelength of the LEDs. Since the wavelength of LEDs actually manufactured can vary, a resistor is placed in the sensor with the value of the resistor corresponding to the actual wavelength of at least one of the LEDs. When the instrument is turned on, it first applies a current to the coding resistor and measures the voltage to determine the value of the resistor and thus the value of the wavelength of the LED in the probe. A disadvantage of this system is that it is dependent upon an analog amplitude level which can be affected by wiring impedance, noise, etc. Another disadvantage is that considerations of cost and error budget limit the number of distinguishable resistance values that may be employed, so that the amount of information conveyable by this means is limited.

Another method of storing coded information regarding the characteristics of the LEDs is shown in U.S. Pat. No. 4,942,877. This patent discloses using an EPROM memory to store digital information, which can be provided in parallel or serially from the sensor probe to the remote oximeter. This system either requires more wires to read the data in parallel, or requires the reading of a multiple, serial bit pattern rather than a single amplitude level as in the system using the resistor. In addition, an oximeter designed to read a resistor would be incompatible with a probe having such an EPROM memory structure.

Other examples of coding sensor characteristics exist in other areas. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another sensor with digital characterization information stored in a PROM, which is read serially using a shift register.

SUMMARY OF THE INVENTION

The present invention provides an encoding mechanism for a medical sensor which uses a modulated signal to provide the coded data to a remote analyzer. The modulated signal could be, for instance, a pulse width modulated signal or a frequency modulated signal. This signal is amplitude independent and thus provides a significant amount of noise immunity.

In a preferred embodiment, the coding is provided in a memory, which is connected to a shift register or counter which produces a pulse width modulated output as it is cycled by a clock. For a pulse oximeter using LEDs, the code would indicate the wavelength of at least one LED. The memory used can be fusible links connected to the inputs of a counter, shift register or other device. The coded information is provided in the duty cycle of the pulse width modulated signal. The averaged duty cycle can be made to match a fixed voltage level for resistors used in existing oximeter probes. In this way, an existing oximeter, which would read an averaged pulse width modulated signal, would think that it is reading a resistor and get the same value. Thus, the probe can be made compatible with oximeters in the field.

The present invention additionally allows multiple types of information to be coded. In addition to the duty cycle in one embodiment, for instance, the pulses could be placed in different time slots within a period to indicate information. Thus, one set of information is indicated by the location of the pulse or pulses, and another set of information by the fraction of time over the period a pulse or pulses are present.

A further understanding of the nature and advantages of the invention may be realized by reference to the remaining portion of the specification and the drawings.

DETAILED DESCRIPTION OF THE PREFERRED EMBODIMENTS

Operation of Prior Art Resistor Calibration

Figure 1:
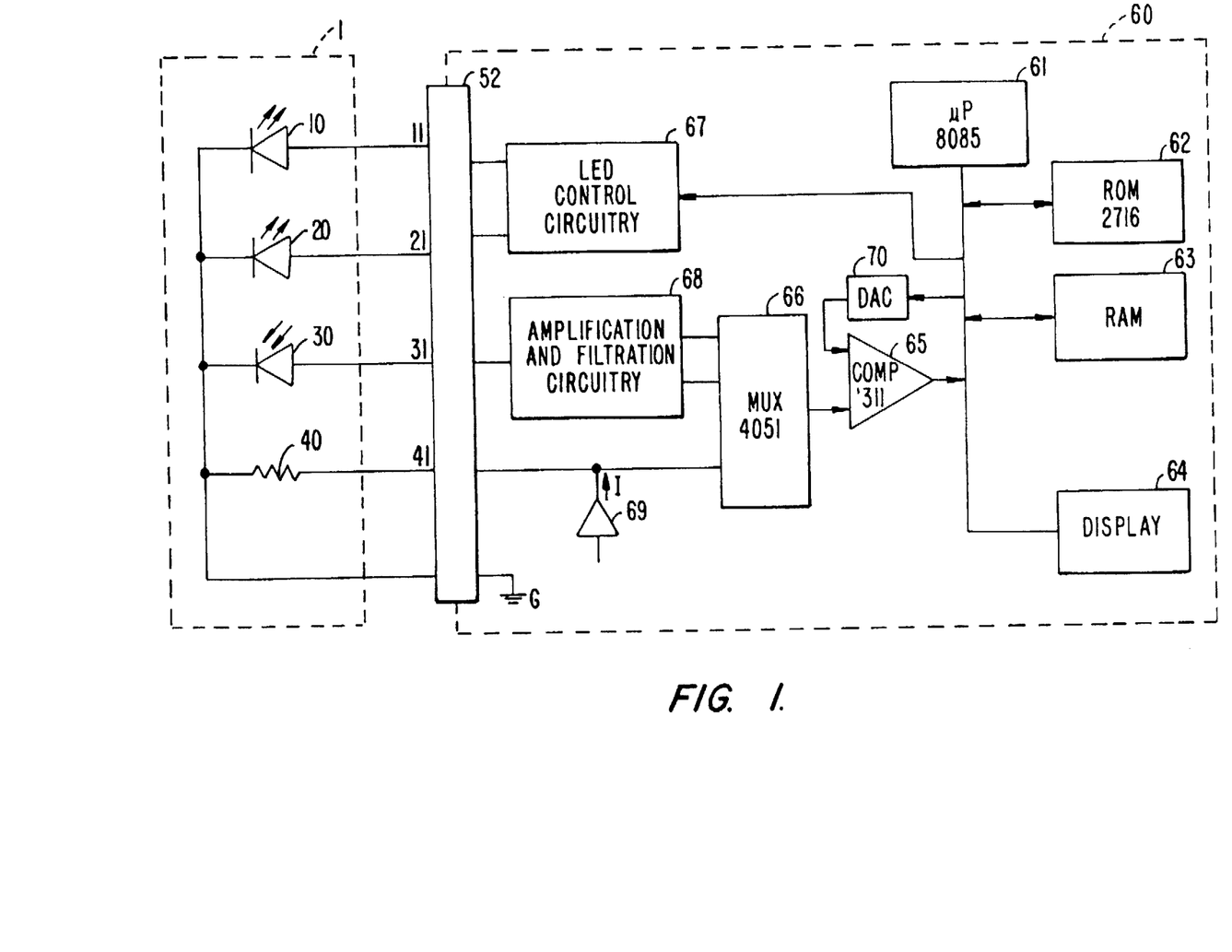
FIG. 1 is a block diagram of a prior art resistor encoding pulse oximeter system.

FIG. 1 illustrates an oximeter probe 1 and an oximeter 60 according to the prior art. Such an oximeter is described in more detail in U.S. Pat. No. 4,700,708, which is incorporated herein by reference. Oximeter 60 contains a microprocessor 61, and a read only memory 62 and random access memory 63. A table of resistances and corresponding coefficients may be easily programmed into ROM 62 at the time oximeter 60 is fabricated.

Figure 9:
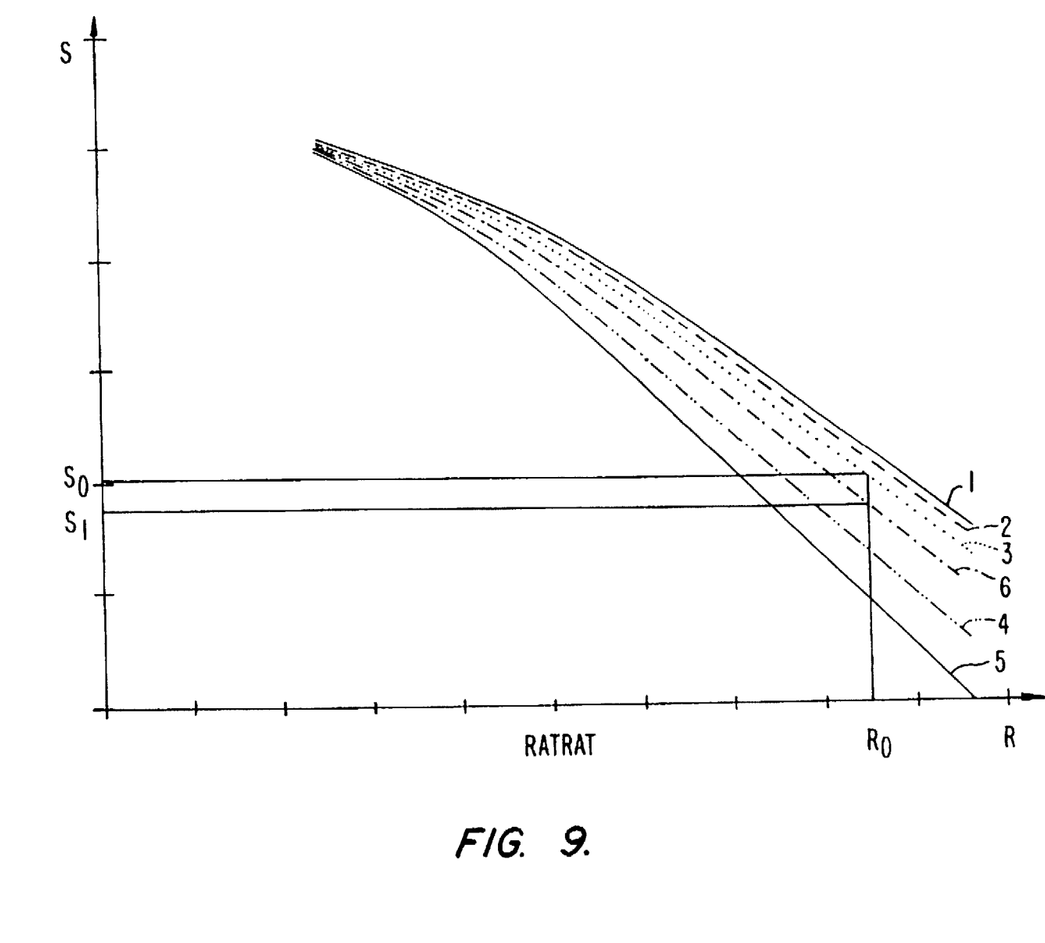
FIG. 9 is an example of a set of curves relating an intermediate value, R, computed by a pulse oximeter, to the oxygen saturation value, S, which the pulse oximeter will report.

When each probe 1 is manufactured, a value for resistor 40 is chosen to correspond to the wavelength of one or both of LEDs 10 and 20. When the probe is then connected to oximeter 60, the value of resistor 40 can be read by oximeter 60. Typically, this resistance corresponds to the wavelength of at least one of the LEDs, and allows the oximeter to look up stored coefficients for a calibration curve corresponding to that wavelength or those wavelengths (FIG. 9 shows examples of these curves). Current I from current source 69 is passed through resistor 40. The resulting voltage is detected at the input of multiplexer 66 and is passed through multiplexer 66 through comparator 65, to microprocessor 61. The analog value presented to the input of comparator 65 is compared to a series of different analog values from digital to analog converter 70. When there is a match at the output of comparator 65, microprocessor 61 knows which digital input to DAC 70 produced this match, and thus the digitally encoded value of the analog voltage produced by resistor 40.

Microprocessor 61 may be programmed to calculate the resistance of resistor 40 and thereafter to look up the coefficients of the calibration curves for the wavelengths of LEDs 10, 20 from a table in ROM 62. Microprocessor 61 is also programmed to itself use the coefficients in its oxygen saturation calculations. By this means, it is not required to recalibrate by hand oximeter 60 for each new probe 1 nor, alternatively, to require that LEDs 10, 20 be of precisely standardized wavelengths.

The specific function and design of the circuitry schematically illustrated in FIG. 1 is seen as obvious when taken in combination with the general description of its function. The function of microprocessors and read only memories are well known and understood and it is well within the capability of a person with ordinary skill in the art to design and program microprocessor 61 to calculate the resistance of resistor 40 and thereby obtain the coefficients corresponding to the wavelengths of LEDs 10, 20 from a simple lookup table in a ROM 62.

Probe 1 may be used with any number of oximeters, the method of operation of which is well understood and beyond the scope of the teaching of the present invention. An example is found in U.S. Pat. No. 5,078,136, which is incorporated herein by reference. Basically, for each heart beat, fresh arterial blood is pumped into the arterioles and capillaries of, for example, a finger, thereby causing a periodic increase and decrease in light intensity observed by detector 30. The oxygen saturation of hemoglobin in the pulsatile blood may be determined by the oximeter 60. For any known wavelength, there are a number of known calibration coefficients referred to above. Given these coefficients and measuring the intensity of diffused light received by detector 30, the oxygen saturation can be computed and displayed.

Microprocessor 61, through LED control circuitry 67, operates LEDs 10, 20. Light from LEDs 10, 20 results in current in detector 30 which passes through amplification and filtration circuitry 68 to multiplexer 66. Comparator 65 and a digital to analog converter 70 are operative as an analog to digital converter means to present a digital signal to the microprocessor 61, thereby allowing microprocessor 61 to determine oxygen saturation and/or pulse rate. Results are shown on display 64.

Present Invention Modulation Encoding

Figure 2:
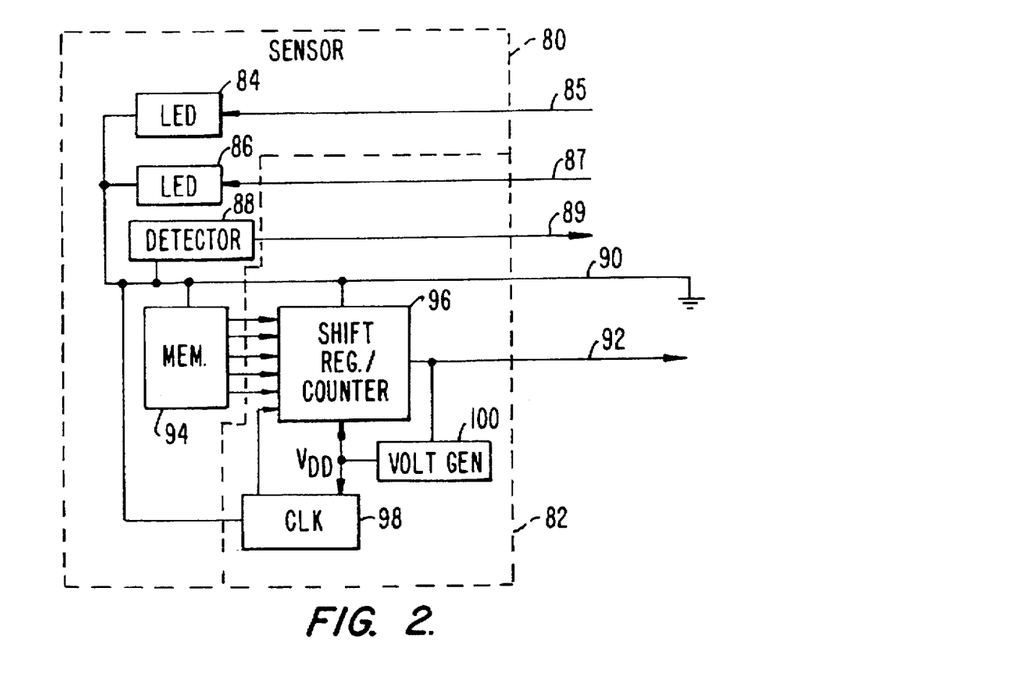
FIG. 2 is a block diagram of a sensor according to the present invention.

FIG. 2 shows a sensor 80 with an innovative Memory Readout Circuit 82 according to one embodiment of the present invention. Alternately, the sensor and Memory Readout Circuit could be separate. The Memory Readout Circuit could be in an ASIC built into the sensor head, in the sensor connector, in a patient module, or in an oximeter instrument box. The sensor includes two LEDs 84 and 86 connected by lines 85 and 87, respectively, to a remote oximeter. A photodetector 88 detects light which is not absorbed by the patient's tissue and provides a signal on a line 89 to the remote oximeter. Also shown is a ground wire 90 and a calibration line 92 (corresponding to the line used to connect to the calibration resistor of the prior art). In this embodiment of the present invention, a memory 94 is provided, coupled to a triggerable pulse pattern generator 96 (shift register or counter). Also included is a clock 98.

In operation, when the circuit of FIG. 2 is provided with a voltage VDD from a voltage generator 100, the clock starts cycling the shift register or counter 96 which has an initial input provided by memory 94. This initial input determines the count and thus the duty cycle provided on serial output line 92. The duty cycle will indicate the value of at least one of the LEDs. Thus, on assembly, the memory is programmed to correspond to the value of the LEDs used. This duty cycle signal could be continuously generated, or only generated for a short time in response to an interrogating signal from the oximeter. The interrogating signal could be an enable signal applied to the clock or counter.

Figures 3, 4:
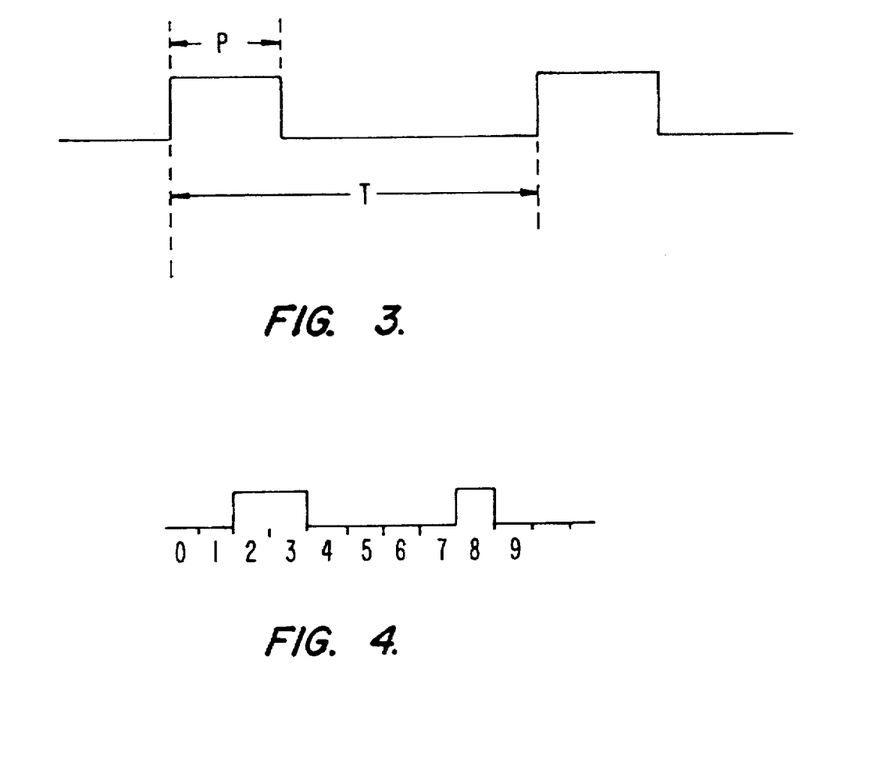
FIG. 3 is a timing diagram illustrating pulse width modulation according to the present invention.
FIG. 4 is a timing diagram illustrating time slot encoding according to the present invention.

An illustration of the output signal is shown in FIG. 3, wherein a pulse width modulated signal with a period T is shown. The signal is high for a portion of time P. Thus, the duty cycle of the signal is P/T. The duty cycle can be made to correspond to the wavelength of at least one of the LEDs used. For instance, duty cycles ranging from 1% to 100% can correspond to related increments in the wavelength of the LED.

The voltage generator 100 of FIG. 2 receives its power from a current provided from the oximeter on line 92. Alternatively, the pulsing of LEDs by the oximeter could provide the power to send the pulse modulated signal back to the oximeter monitor on line 92. Alternately, a battery could be used or a separate Memory Readout Circuit module could have its own power supply connection. By putting the power supply, shift register and clock elements in a separate Memory Readout Circuit module, the sensor can be made disposable while still being relatively inexpensive. Alternately, an ASIC design could be generated which would make the entire Memory Readout Circuit 82 very inexpensive. In this case it could be economical to include circuit 82 as part of every sensor assembly, even when sensors are designed to be disposable.

In addition to the pulse width modulation, information could be encoded, in an alternate embodiment, by the location of the pulses within a period. FIG. 4 illustrates an example of a period having ten time slots, with pulses occurring in time slots 2, 3 and 8. The location of the pulses can indicate certain information which is different from the information conveyed by the duty cycle of the signal. The example in FIG. 4 has a duty cycle of 30%. In one example, the duty cycle could indicate the wavelength of an LED, while the location of the pulses in the time slots might indicate the brand or type of sensor being used, such as a finger sensor, a nose bridge sensor, etc. In another example, the second type of information could be the wavelength of a second LED. With the single resistor of the prior art, the resistor had to convey either the combined wavelength values of the two LEDs, or the wavelength value of one LED. The additional information provided by this invention could improve the accuracy of the calibration coefficients determined by the oximeter, because more information about the sensor would be known to the oximeter.

Yet another example of the potential uses of the additional information-carrying capacity of the digital code would arise if a manufacturer wished to introduce special sensors incorporating three or more LEDs of different wavelengths, in addition to the more common sensors having LEDs of only two wavelengths. The number of LEDs present could be indicated by the digital code, so that the instrument could select an appropriate strategy for operating the LEDs and interpreting the light pulses seen by the detector.

Figure 5:
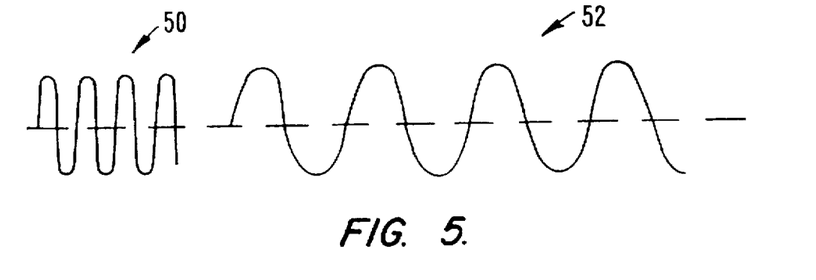
FIG. 5 is a diagram illustrating frequency modulation according to the present invention.

FIG. 5 shows an alternate method for transmitting modulated information. A frequency generator could be used with the frequency being related to the wavelength of the LED or other characteristic of a transducer in the sensor. FIG. 5 illustrates a first portion 50 with a wavelength with a high frequency, indicating one coded value, and a second portion 52 with a low frequency indicating a different coded value. Such a signal could be generated with a current-to-frequency converter, for instance. The current provided to the input of the converter could be controlled by a memory, or resistor which is used to vary the value of a current source.

Figure 6:
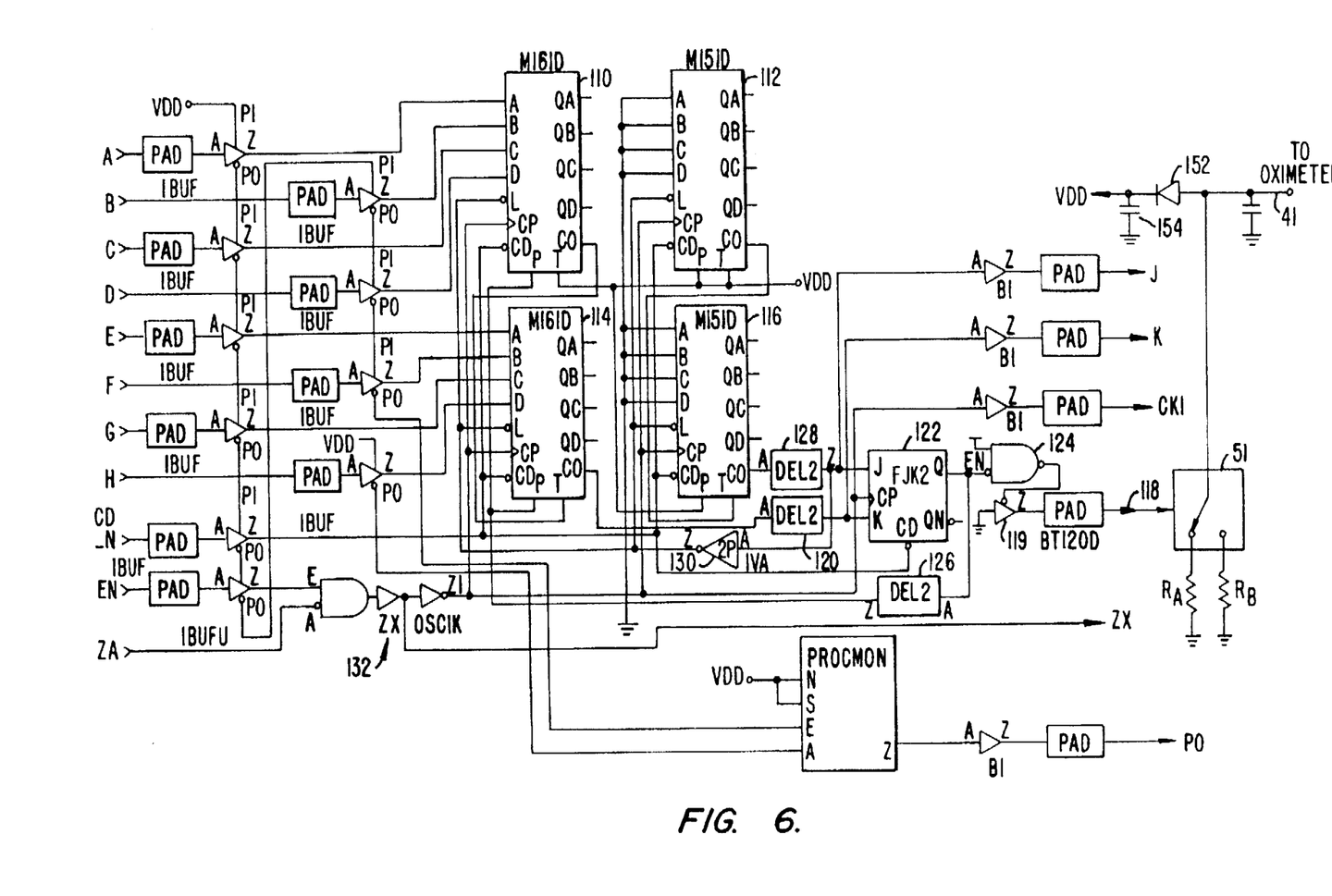
FIG. 6 is a detailed circuit diagram of one embodiment of a sensor according to FIG. 2.

FIG. 6 is a circuit diagram of one embodiment of a portion of the sensor circuitry of FIG. 2. The block diagram shows an application specific integrated circuit (ASIC) design. The design uses four counters, counters 110, 112, 114 and 116. Input lines A to H can come from an external memory to the pads connected to the parameter input (PI) lines, or, a fusible link or other coding mechanism can be connected to each of the input lines. Counters 110 and 114 are connected in series to provide a first count. The time it takes for counters 110 and 114 to progress from their initially set count to the capacity of the counters (255) will define the high portion of the pulse on output 118. The starting count of counters 110 and 114 is defined by the inputs A–H, which are programmable in accordance with the wavelength of the LED placed in the individual sensor.

Counters 112 and 116 are connected in series, with the inputs grounded. The amount of time between when the first two counters (110, 114) reach their full count and when the second two counters (112, 116) reach their full count will define the low portion of the output pulse on line 118.

When first set of counters 110 and 114 reach their maximum count, the carry out signal of counter 114 passes through a delay circuit 120 to the K input of flip-flop 122. The delay is provided to ensure that the clock arrives at flip-flop 122 first. This causes the Q output to go low, which propagates through NAND gate 124 to output line 118. This defines the end of the high portion of the pulse width output. The low output is also provided as a feedback through delay line 126 to the parallel enable input (P) of counters 110 and 114 to disable further counting of these counters until the next period.

Counters 112 and 116 will have started their count at the same time as the other counters, but will count to a full count from 0. When the full count is reached, the carry out output of counter 116 is provided through a delay line 128 to the J input of flip-flop 122. This causes the Q output to go high, defining the end of the low period of the pulse width output on line 118. This output is also provided as a feedback through inverter 130 to the load input (L) of all the counters. This will reload the initial counts into all the counters to start the cycle over again. When the first set of counters reach the top of their count, this will define the end of the high portion of the duty cycle again.

The counters receive their clock from an oscillator circuit 132. A precise clock is not needed since the high and low portions of the ultimate output signal will be equally affected by the clock frequency, and thus variations in the clock's frequency will not affect the duty cycle, which encodes the information. This allows the circuit to be made relatively inexpensively.

Similar immunity to variations in clock frequency can be achieved when digital information is to be communicated, as in the waveform of FIG. 4. The oximeter could be programmed to calculate the actual clock rate by detecting the repeating pattern. Alternately, the clock frequency can be detected by requiring that every permitted code string begin with a regular series of ON/OFF pulses, so that the instrument can recognize the clock frequency.

The other pins and circuits are basically for test purposes. The $CD_{13}$ N, EN and ZA signals on the left of the diagram are test inputs, as are the J, K and CKI signals on the right.

The PROCMON circuit is a process monitor cell used in testing the ASIC.

Figure 7:
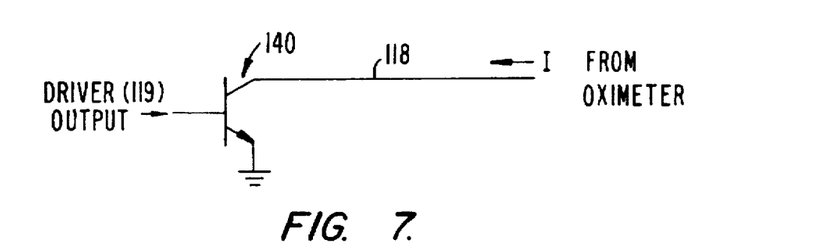
FIG. 7 is a diagram of an open collector output stage for the circuit of FIG. 6.

As can be seen, output line 118 is driven by NAND gate 124 to provide a pulse width modulated output. If this is hooked up to an existing oximeter input, such as input line 41 of the oximeter of FIG. 1, this will meet a circuit 69 which provides a current to this line. One way to make the circuit backward compatible is to use an open collector output for an output driver 119 such as shown in FIG. 7. As shown in FIG. 7, the driver 119 output would connect to the base of a transistor 140, with a collector of transistor 140 being provided to output 118 which would connect to input 41 of FIG. 1. The current provided from the oximeter would thus have nowhere to go, indicating a very high resistance, when transistor 140 is turned off due to line 118 being low. When line 118 is high, the current will go to ground, indicating a short. The effective voltage or average voltage seen by the oximeter monitor will be the duty cycle times the maximum voltage provided on line 41 by the circuitry of the oximeter monitor 60 of FIG. 1.

Alternately, a separate switch S1 as shown in FIG. 6 could be used. The switch alternately connects between two resistance values, $R_A$ and $R_B$. Switch S1 could be implemented, for example, as a pair of field effect transistors (FET's). One FET could be responsive to a high level signal from driver 119, while the other FET would be responsive to a low level signal. These could also be implemented as part of the outputs of driver 119 itself. Such a circuit has an advantage where an infinite or zero impedance is undesirable for the reading circuit in the oximeter itself, as discussed below.

Figure 8A:
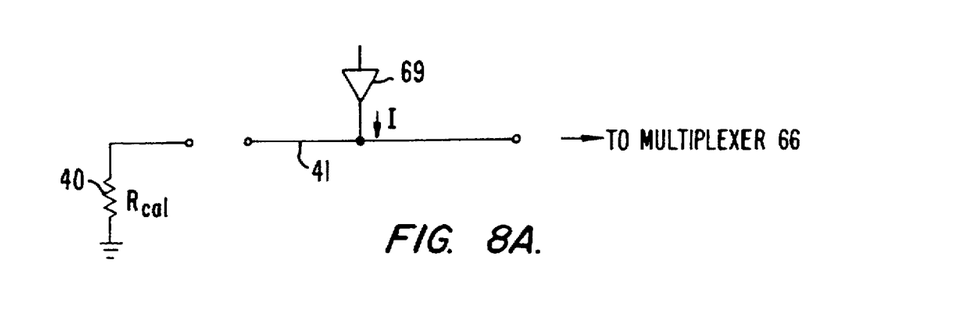
FIGS. 8A and 8B are diagrams of two alternative resistance-reading circuits.
Figure 8B:
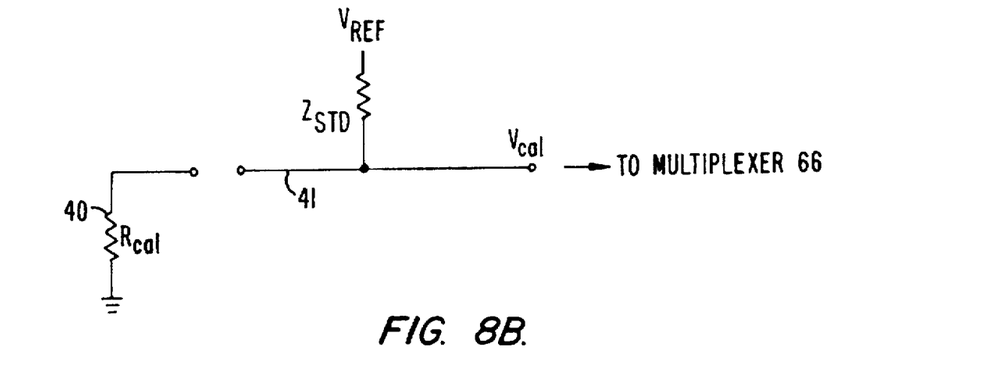

FIGS. 8A and 8b show block diagrams for two alternative circuits which may be used in the oximeter monitor to read the value of calibration-indicating resistor 40, which is commonly known as Rcal. In FIG. 8A appears the same type of circuit that is also shown in FIG. 1. Current source 69 sends a known current I through resistor 40, and the resulting voltage is passed to a multiplexer, which in turn will deliver the voltage to an analog-to-digital converter, which will produce a digital value proportional to the voltage. The digital value can then be interpreted by microprocessor 61 to determine the value of resistor 40. A disadvantage of this method is that part of the error budget (margin for error) for reading of resistor 40 will be consumed by errors in the value of current I and errors in reading the resulting voltage.

FIG. 8B shows a method which eliminates these contributions to the error budget. A reference voltage Vref is applied to the series combination of a standard impedance Zstd and Rcal resistor 40 which is to be measured. The resulting voltage across Rcal, which is labelled Vcal in FIG. 8B, is fed to a multiplexer, and from there to an analog to digital converter. By one of several known means, microprocessor 61 then gains information as to the ratio of Vcal to Vref. One such means is to apply Vref to the reference input of the analog to digital converter, so that Vref becomes the reference voltage used by the analog to digital converter. The output of the ADC will then automatically represent the ratio of Vcal to Vref. Alternatively, an analog to digital converter may separately measure the values of Vcal and Vref, using some third voltage as a reference, and the two resulting readings may be delivered to microprocessor 61. Microprocessor 61 can then determine the ratio by digital division.

In the description of FIG. 2, it was explained that a function of Memory Readout Circuit 82 is to cause alternation of the voltage level on Rcal readout line 41, between high and low states, in accordance with the pattern stored in memory 94. FIG. 6 schematically shows an output circuit that may be incorporated in Memory Readout Circuit 82, in order to accomplish this alternation. Switching element S1, (which may, for example, be implemented using two FET's) switches line 41 alternately between two alternate resistance values, $R_A$ and $R_B$. Either of these resistance values may be selected to be zero (i.e. a short circuit to ground) or an open circuit (i.e. a quasi-infinite resistance).

When the output circuit of FIG. 6 is to be used with the readout circuit of FIG. 8A, resistors $R_A$ and $R_B$ are restricted to being finite or zero (i.e. not an open circuit), since the voltage created by current source 69 across a quasi-infinite resistance would be undefined. When the readout circuit is to be of the form shown in FIG. 8B, this restriction to finite values is not necessary.

Now consider how the duty cycle of the output of Memory Readout Circuit 82 may be selected, so as to simulate the value of a particular value of Rcal. Define $f_A$ as the fraction of time during one full readout cycle that the switch is connected to resistor $R_A$, and $f_B$ as the fraction of time that the switch is connected by resistor $R_B$. By design, $f_A+f_B=1$. First take the case of the current-source readout of FIG. 8A. When current I from source 69 is applied to the circuit of FIG. 6, the mean voltage that appears on line 41 will be $I(f_A R_A + f_B R_B)$. So, for example, if $R_B=0$, a selected resistance $R_S$ can be simulated by choosing $f_A = R_S/R_A$. To provide a more specific example, if the resistance to be simulated is 6.04 KΩ, $R_A=10.0$ KΩ, and $R_B=0$, then the appropriate value of $f_A$ will be 0.604.

In order to eliminate the effect of normal statistical variations in values of $R_A$ during manufacturing, it may be desirable to simulate a particular resistance not by selecting a particular value of $f_A$, but rather by selecting $f_A$ at the time of manufacturing so that the product $f_A R_A$ has the desired value. Thus two different manufactured devices might simulate the same effective resistance, even though they would have different values of $f_A$.

Next, consider the selection of appropriate values of $f_A$ and $f_B$ when the readout circuit of FIG. 8B is to be used. If Zstd is a pure resistance, having a value of Rstd, the mean voltage developed on line 41 will be $$Vmean=Vref\{f_A[R_A/(R_A+Rstd)]+f_B[R_B/(R_B+Rstd)]\}$$

The simulation circuit retains the virtue inherent in the design of the readout circuit of FIG. 8B, which is that statistical variations in Vref need not affect the error budget of reading Rcal (or a simulated Rcal value), so long as the value of Vmean is read ratiometrically.

As one example of the selection of $f_A$ to simulate a particular value of Rcal, when the circuit of FIG. 8B is employed, consider the case in which we set $R_B=0$. To simulate a particular resistance value Rs, we require:

$$Rs/(Rs+Rstd)=f_A[R_A/(R_A+Rstd)].$$

Therefore $f_A=(Rs/R_A)(R_A+Rstd)/(R_s+Rstd)$.

For example, if $Rstd=R_A=10.0$ KΩ, and if the value of Rs to be simulated is 6.04 KΩ, then $f_A=0.753$. If $R_A=10.0$ KΩ and Rstd=7.5 KΩ, then we would require a different value, $f_A=0.781$. A version of Memory Readout Circuit 82 could be manufactured which would properly simulate a predetermined value of Rcal for several different values of Rstd, such as might be encountered in different design generations of instruments. To accomplish this end, it would produce different values of $f_A$ depending on the value of Rstd. Circuit 82 could include a state machine or processor programmed to determine the value of Rstd by any method equivalent to the following sequence of steps:

1. Observe the open circuit value of applied voltage, which would be Vref;
2. observe the current I which flows when its output line is connected through a finite or zero resistance $R_K$ to ground; and 3. compute $Rstd = \dfrac{Vref}{I} - R_K$ As in the case of the current-source readout of FIG. 8A, it would be possible to establish the value (or values) of $f_A$ at time of manufacture, to correct for statistical variability in the values of $R_A$ and $R_B$.

The voltage supply VDD can be provided to the circuit of FIG. 6 from the current provided by the oximeter on its output line 41 of FIG. 1. This is shown in FIG. 6 where line 41 connects to output 118 through a resistor 150. A diode 152 and capacitor 154 are added to provide a supply voltage VDD from the current generated by the oximeter to read the value of the "resistor" the oximeter expects to see. Resistor 150 is provided to limit the current flow.

The memory for encoding of a pulse width (or frequency for frequency modulation) can be provided in a number of different ways. Programmable links connected to data lines can be programmed at the time each LED is placed into a sensor during manufacturing. Alternately, a memory chip can be programmed to correspond to the LED value. Alternately, a set of, say, 20 pre-programmed memory chips can be available, with the assembler picking the one having the code which most closely represents the measured wavelength of the LED.

One advantage of sensors made according to this invention is that they can be designed to be back-compatible with early-generation instruments, while offering new capabilities when used in combination with new instruments. For example, oximeters made according to U.S. Pat. No. 4,700, 708 are designed to recognize an identifying resistor, such as resistor 40 in FIG. 1, whose value instructs the oximeter to select a particular calibration curve from among a set of possible curves whose defining coefficients are stored in ROM.

For example, FIG. 9 shows a set of curves relating an intermediate computed value, called R, to the final value, S, of oxygen saturation, which is to be delivered by an oximeter. The third of a set of five possible curves has been selected, in accordance with the value of an identifying resistor, and has been used to compute from particular value $R_O$ a saturation value $S_O$. Five curves are shown for ease of illustration, 21 curves is more desirable. Also shown in FIG. 9 is dashed line 6. This is a calibration curve for a hypothetical newly-designed sensor. While old sensors may use 21 curves, curve 6 could be, for instance, one of a hundred more accurate curves for newer sensors. Curve 6 does not exactly match any of standard curves 1 through 5. It would be possible to choose a digital pattern for this sensor such that its duty cycle would simulate resistor number 3 (so that existing oximeters would assign best-match curve 3 to the sensor). Meanwhile, many different digital codes would be available, all of which would have the same percentage ON time, which could be used to communicate to properly-designed newer instruments a choice among a much larger variety of standard curves, one of which might be substantially identical to curve 6. This could be done, for example, by using the pulse placement method described in FIG. 4.

It would also be possible to use the available alternative codes to communicate numerical correction terms to the standard curves stored in ROM. For example, curve 6 could be represented as a modification of curve 3 by the coefficients a, b, and c:

$$S(R)=S_3(R)+a+bR+cR^2$$

With this correction, the input value $R_0$ would cause an early-generation oximeter to compute approximate saturation value $S_0$, while a more modern oximeter could deliver the more accurate value $S_1$, as shown in FIG. 9.

Yet another way to use the extra coding dimension just described is as an identifier of the manufacturer of a sensor. A digital code to identify the sensor manufacturer could be selected from among the many different possible codes having a desired average duty cycle, and employed in a number of alternative ways. For example, a manufacturer could design an instrument so that it would not operate unless it recognized the code corresponding to sensor made by the same manufacturer. This could be a useful means of ensuring only sensors with certain characteristics are used, or to ensure sensor quality control, patient safety, and efficacy of performance.

As will be understood by those familiar with the art, the present invention may be embodied in other specific forms without departing from the spirit or essential characteristics thereof. For example, frequency modulation can be used instead of pulse width modulation. This could be done with a current-to-frequency converter or with an oscillator. Alternately, resistor values could be used to provide the coded memory information. Accordingly, the disclosure of the preferred embodiment of the invention is intended to be illustrative, but not limiting, of the scope of the invention which is set forth in the following claims.

What is claimed is:

1. A pulse oximeter sensor comprising:
    a first emitter which emits light of a first known wavelength;
    a photosensor for sensing the light emitted by the first emitter;
    a transmitter for coupling said sensor to a remote oximeter;
    an encoder for encoding a value indicative of said first known wavelength as a coded value;
    a modulator, coupled to said transmitter, for providing said coded value as a modulated signal to said transmitter, wherein said transmitter is adapted to transmit said modulated signal to said remote oximeter for use in an oxygen saturation measurement.

2. The sensor of claim 1 wherein said encoder includes a memory having a multiple bit output and means, coupled to said memory, for generating a repeating pulse pattern.

3. The sensor of claim 2 wherein said memory comprises a series of fusible links.

4. The sensor of claim 2 wherein said means for generating a repeating pulse pattern comprises at least one counter.

5. The sensor of claim 2 wherein said means for generating a repeating pulse pattern comprises a shift register.

6. The sensor of claim 2 wherein said means for generating a repeating pulse pattern includes an oscillator.

7. The sensor of claim 1 wherein said transmitter includes an output circuit for sinking a current received on an input of said sensor from said remote oximeter.

8. The sensor of claim 7 further comprising a voltage supply, coupled to said output circuit, for generating, from said current from said remote oximeter, a supply voltage for said encoder.

9. The sensor of claim 8 wherein said voltage supply means includes a filter coupled to said output circuit.

10. The apparatus of claim 1, further comprising means for switching an output of said sensor between first and second resistances to generate a pulse width modulated signal.

11. The apparatus of claim 1 wherein said transmitter is a cable.

12. A method for supplying a wavelength of a light emitter in a pulse oximeter transducer with a light emitter and photosensor to a pulse oximeter monitor, comprising the steps of:
    encoding a value indicative of a wavelength of said light emitter as a modulated signal; and transmitting said modulated signal to said pulse oximeter monitor.

13. The method of claim 12 wherein said modulated signal is a pulse width modulated signal.

14. The method of claim 12 wherein said encoding step includes storing in a memory an indication of a characteristic of said transducer.

15. The method of claim 14 wherein said step of storing includes storing multiple digital bits in said memory.

* * * * *

UNITED STATES PATENT AND TRADEMARK OFFICE
CERTIFICATE OF CORRECTION

PATENT NO. : 5,779,630
DATED : July 14, 1998
INVENTOR(S) : Michael E. Fein et al.

It is certified that error appears in the above-identified patent and that said Letters Patent is hereby corrected as shown below:

On the title page item:

[62] Division of Ser. No. 168,449, Dec. 17, 1993, Pat No. 5,695,059 should read:

[62] Division of Ser. No. 168,449, Dec. 17, 1993, Pat. No. 5,645,059.

Signed and Sealed this

Thirteenth Day of April, 1999

Attest:

Q. TODD DICKINSON

*Attesting Officer*     *Acting Commissioner of Patents and Trademarks*